US008999657B2

(12) United States Patent
Shelley et al.

(10) Patent No.: US 8,999,657 B2
(45) Date of Patent: Apr. 7, 2015

(54) REAGENTS, METHODS, AND KITS FOR THE CLASSIFICATION OF CANCER

(71) Applicant: Gundersen Lutheran Health System, La Crosse, WI (US)

(72) Inventors: Carl S. Shelley, La Crosse, WI (US); Steven E. Cash, La Crosse, WI (US); Jeremiah J. Andersen, La Crosse, WI (US); Qiangwei Fu, La Crosse, WI (US)

(73) Assignee: Gundersen Lutheran Health System, La Crosse, WI (US)

( * ) Notice: Subject to any disclaimer, the term of this patent is extended or adjusted under 35 U.S.C. 154(b) by 0 days.

(21) Appl. No.: 13/855,365

(22) Filed: Apr. 2, 2013

(65) Prior Publication Data
US 2013/0259877 A1 Oct. 3, 2013

Related U.S. Application Data

(60) Provisional application No. 61/790,898, filed on Mar. 15, 2013, provisional application No. 61/619,002, filed on Apr. 2, 2012.

(51) Int. Cl.
*G01N 33/574* (2006.01)
*G01N 33/68* (2006.01)

(52) U.S. Cl.
CPC ...... *G01N 33/6893* (2013.01); *G01N 33/57423* (2013.01); *G01N 33/57484* (2013.01)

(58) Field of Classification Search
None
See application file for complete search history.

(56) References Cited

U.S. PATENT DOCUMENTS 7,674,605 B2 3/2010 Lin et al.
2006/0216231 A1 9/2006 Shelley et al.

FOREIGN PATENT DOCUMENTS

| EP | 0339695 | 11/1989 |
| GB | 2188638 | 10/1987 |
| WO | PCT/GB85/00392 | 9/1985 |
| WO | WO9007861 | 7/1990 |

OTHER PUBLICATIONS

Ioachim et al. (Int. J. Cancer: Supplement 8, 132-133, 1994).*
Fernandez-Rodriguez, Julia, et al., "The Leukocyte Antigen CD43 Is Expressed in Different Cell Lines of Nonhematopoietic Origin," Tumor Biology (Apr. 12, 2002), pp. 193-201, vol. 23.
Andersson CX et al., CD43 has a functional NLS, interacts with β-catenin, and affects gene expression. *Biochem Biophys Res Commun.* 2004;316:12-17.
Ardman B et al., CD43 interferes with T-lymphocyte adhesion. *Proc Natl Acad Sci USA.* 1992;89:5001-5.
Bazil V et al., CD43, the major sialoglycoprotein of human leukocytes, is proteolytically cleaved from the surface of stimulated lymphocytes and granulocytes. *Proc Natl Acad Sci USA.* 1993;90:3792-6.
Brown WRA et al., Identification of a glycoprotein-like molecule at the cell surface of rat thymocytes. *Nature.* 1981;289:456-60.
Brown TJ et al., Characterization of a CD43/leukosialin-mediated pathway for inducing apoptosis in human T-lymphoblastoid cells. *J Biol Chem.* 1996;271:27686-95.
Campanero MR et al., Down-regulation by tumor necrosis factor-α of neutrophil cell surface expression of the sialophorin CD43 and the hyaluronate receptor CD44 through a proteolytic mechanism. *Eur J Immunol.* 1991;21:3045-8.
Cyster JG et al., The dimensions of the T-lymphocyte glycoprotein leukosialin and identification of linear protein epitopes that can be modified by glycosylation. *EMBO J.* 1991;10:893-902.
Da Silva N et al., HnRNP-K and Purα act together to repress the transcriptional activity of the CD43 gene promoter. *Blood.* 2002;100:3536-44.
Fu, Qiangwei et al., CD43 in the nucleus and cytoplasm of lung cancer is a potential therapeutic target, *Int. J. Cancer:* 132, 1761-1770 (2013).
Fukuoka M et al., Antiadhesive function of 130-kd glycoform of CD43 expressed in CD4 T-lymphocyte clones and transfectant cell lines. *Blood.* 2000;96:4267-75.
He Y-W, et al., High level expression of CD43 inhibits T cell receptor/CD3-mediated apoptosis. *J Exp Med.* 1999;190:1903-8.
Hernandez JD et al., Galectin-1 binds different CD43 glycoforms to cluster CD43 and regulate T cell death. *J Immunol.* 2006;177:5328-36.
Ioachim HL et al., Reactivity of lung tumors with lung-derived and non-lung-derived monoclonal antibodies. *Int J Cancer: Suppl.* 1994;8:132-3.
Kim HJ et al., CD43 cross-linking increases the Fas-induced apoptosis through induction of Fas aggregation in Jurkat T-cells. *Exp Mol Med.* 2006;38:357-63.
Mambole A et al., The cleavage of neutrophil leukosialin (CD43) by cathepsin G releases its extracellular domain and triggers its intramembrane proteolysis by presenilin/γ-secretase. *J Biol Chem.* 2008;283:23627-35.

(Continued)

Primary Examiner — Brad Duffy
Assistant Examiner — Nelson B Moseley, II
(74) Attorney, Agent, or Firm — Charles S. Sara, Esq.; Daniel A. Blasiole; DeWitt Ross & Stevens SC

(57) ABSTRACT

Reagents, methods, and kits for the classification of cancer that comprise or employ antibodies that bind specific regions of CD43. One method includes contacting tissue with an antibody capable of specifically binding the cytoplasmic tail of CD43, contacting the tissue with an antibody capable of specifically binding the extracellular domain of CD43, and resolving cellular localization of any binding to the tissue with the antibody capable of specifically binding the cytoplasmic tail of CD43 and the antibody capable of specifically binding the extracellular domain of CD43. The binding patterns of the antibodies can be used to characterize cancer as more aggressive or less aggressive and can distinguish small cell lung cancer from non-small cell lung cancer. The cancer may therefore be treated in accordance of the characterization.

19 Claims, 3 Drawing Sheets

(56) References Cited

OTHER PUBLICATIONS

Matsumoto M et al., CD43 functions as a ligand for E-selectin on activated T cells. *J Immunol.* 2005;175:8042-50.

Ostberg JR et al., The Roman god Janus: A paradigm for the function of CD43. *Immunol Today.* 1998;19:456-550.

Pallant A et al., Characterization of cDNAs encoding human leukosialin and localization of the leukosialin gene to chromosome 16. *Proc Natl Acad Sci USA.* 1989;86:1328-32.

Piller F et al., Human T-lymphocyte activation is associated with changes in O-glycan biosynthesis. *J Biol Chem.* 1988;263:15146-50.

Remold-O'Donnell E et al., Proteolytic fragmentation of sialophorin (CD43). Localization of the activation-inducing site and examination of the role of sialic acid. *J Immunol.* 1990;145:3372-8.

Remold-O'Donnell E et al., Characterization of a human lymphocyte surface sialoglycoprotein that is defective in Wiskott-Aldrich syndrome. *J Exp Med.* 1984;159:1705-23.

Rosenstein Y et al., CD43, a molecule with multiple functions. *Immunol Res.* 1999;20:89-99.

Rosenstein Y et al., CD43, a molecule defective in Wiskott-Aldrich syndrome, binds ICAM-1. *Nature.* 1991;354:233-5.

Sabri S et al., Glycocalyx modulation is a physiological means of regulating cell adhesion. *J Cell Sci.* 2000;113:1589-600.

Santamaría M et al., Specific monoclonal antibodies against leukocyte-restricted cell surface molecule CD43 react with nonhematopoietic tumor cells. *Cancer Res.* 1996;56:3526-9.

Sánchez-Mateos P et al., Regulatory role of CD43 leukosialin on integrin-mediated T-cell adhesion to endothelial and extracellular matrix ligands and its polar redistribution to a cellular uropod. *Blood.* 1995;86:2228-39.

Seethala RR et al., The selective expression of CD43 in adenoid cystic carcinoma. *Appl Immunohistochem Mol Morphol.* 2008;16:165-72.

Seo W et al., CD43 processing and nuclear translocation of CD43 cytoplasmic tail are required for cell homeostasis. *Blood.* 2009;114:3567-77.

Serrador JM et al., CD43 interacts with moesin and ezrin and regulates its redistribution to the uropods of T lymphocytes at the cell-cell contacts. *Blood.* 1998;91:4632-44.

Seveau S et al., Neutrophil polarity and locomotion are associated with surface redistribution of leukosialin (CD43), an antiadhesive membrane molecule. *Blood.* 2000;95:2462-70.

Shelley CS et al., During U937 monocytic differentiation repression of the CD43 gene promoter is mediated by the single-stranded DNA binding protein Purα. *Br J Haematol.* 2001;115:159-66.

Shelley CS et al., Molecular characterization of sialophorin (CD43), the lymphocyte surface sialoglycoprotein defective in Wiskott-Aldrich syndrome. *Proc Natl Acad Sci USA.* 1989;86:2819-28.

Sikut R et al., Detection of CD43 (leukosialin) in colon adenoma and adenocarcinoma by novel monoclonal antibodies against its intracellular domain. *Int J Cancer.* 1999;82:52-8.

Sikut R et al., Colon adenoma and cancer cells aberrantly express the leukocyte-associated sialoglycoprotein CD43. *Biochem Biophys Res Comm.* 1997;238:612-6.

Soler M et al., Leukosialin (CD43) behavior during adhesion of human monocytic THP-1 cells to red blood cells. *J Leukoc Biol.* 1997;61:609-18.

Stöckl J et al., Leukosialin (CD43)-major histocompatibility class I molecule interactions involved in spontaneous T cell conjugate formation. *J Exp Med.* 1996;184:1769-79.

Subramanian J et al., Gene expression-based prognostic signatures in lung cancer: Ready for clinical use? *J Natl Cancer Inst.* 2010;102:464-74.

Todeschini AR et al., Costimulation of host T lymphocytes by a trypanosomal trans-sialidase: Involvement of CD43 signaling. *J Immunol.* 2002;168:5192-8.

Tomlinson-Jones A et al., Characterization of the activation-associated isoform of CD43 on murine T lymphocytes. *J Immunol.* 1994;153:3426-39.

van den Berg TK et al., Cutting edge: CD43 functions as a T cell counterreceptor for the macrophage adhesion receptor sialoadhesin (Siglec-1). *J Immunol.* 2001;166:3637-40.

Woo VL et al., Assessment of CD43 expression in adenoid cystic carcinomas, polymorphous low-grade adenocarcinomas, and monomorphic adenomas. *Oral Surg Oral Med Oral Pathol Oral Radiol Endod.* 2006;102:495-500.

\* cited by examiner

CD43 PRECURSOR AMINO ACID SEQUENCE NP_003114

```
  1  MATLLLLLGV LVVSPDALGS TTAVQTPTSG EPLVSTSEPL SSKMYTTSII SDPKADSTGD
 61  QTSALPPSTS INEGSPLWTS IGASTGSPLP EPTTYQEVSI KMSSVPQETP HATSHPAVPI
121  TANSLGSHTV TGGTITTNSP ETSSRTSGAP VTTAASSLET SRGTSGPPLI MATVSLETSK
181  GTSGPPVTMA TDSLETSTGT TGPPVTMTTG SLEPSSGASG PQVSSVKLST MMSPTTSTNA
241  STVPFRNPDE NSRGMLPVAV LVALLAVIVL VALLLWRRR QKRRTGALVL SRGGKRNGVV
301  DAWAGPAQVP EEGAVTVTVG GSGGDKGSGF PDGEGSSRRP TLTTFFGRRK SRQGSLAMEE
361  LKSGSGPSLK GEEEPLVASE DGAVDAPAPD EPEGGDGAAP
```

Residues 1-400:   Precursor protein  
Residues 1-19:    Signal peptide  
Residues 20-400:  Mature peptide  
Residues 20-253:  Extracellular domain (underline)  
Residues 254-276: Transmembrane region  
Residues 277-400: Cytoplasmic tail (bold)  
Residues 375-400: Exemplary peptide sequence used to generate the SSGZ antibody (bold underline)

FIG. 1

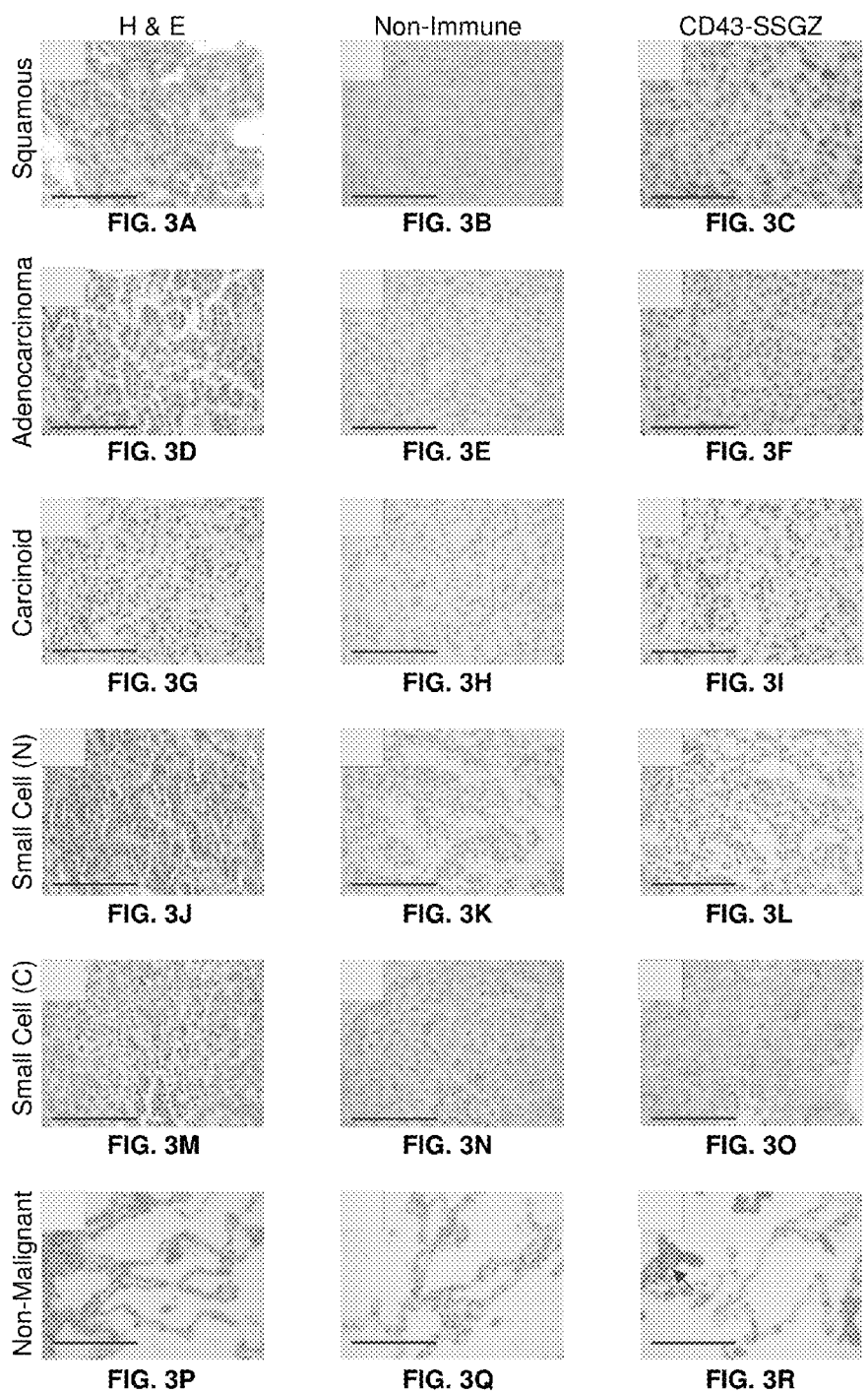

SEQUENCE LISTING

```
<160> NUMBER OF SEQ ID NOS: 1

<210> SEQ ID NO 1
<211> LENGTH: 400
<212> TYPE: PRT
<213> ORGANISM: Homo sapiens

<400> SEQUENCE: 1

Met Ala Thr Leu Leu Leu Leu Gly Val Leu Val Val Ser Pro Asp
1               5                   10                  15

Ala Leu Gly Ser Thr Thr Ala Val Gln Thr Pro Thr Ser Gly Glu Pro
            20                  25                  30

Leu Val Ser Thr Ser Glu Pro Leu Ser Ser Lys Met Tyr Thr Thr Ser
        35                  40                  45

Ile Thr Ser Asp Pro Lys Ala Asp Ser Thr Gly Asp Gln Thr Ser Ala
    50                  55                  60

Leu Pro Pro Ser Thr Ser Ile Asn Glu Gly Ser Pro Leu Trp Thr Ser
65                  70                  75                  80

Ile Gly Ala Ser Thr Gly Ser Pro Leu Pro Glu Pro Thr Thr Tyr Gln
                85                  90                  95

Glu Val Ser Ile Lys Met Ser Ser Val Pro Gln Glu Thr Pro His Ala
            100                 105                 110

Thr Ser His Pro Ala Val Pro Ile Thr Ala Asn Ser Leu Gly Ser His
        115                 120                 125

Thr Val Thr Gly Gly Thr Ile Thr Thr Asn Ser Pro Glu Thr Ser Ser
    130                 135                 140

Arg Thr Ser Gly Ala Pro Val Thr Thr Ala Ala Ser Ser Leu Glu Thr
145                 150                 155                 160

Ser Arg Gly Thr Ser Gly Pro Pro Leu Thr Met Ala Thr Val Ser Leu
                165                 170                 175

Glu Thr Ser Lys Gly Thr Ser Gly Pro Pro Val Thr Met Ala Thr Asp
            180                 185                 190

Ser Leu Glu Thr Ser Thr Gly Thr Thr Gly Pro Pro Val Thr Met Thr
        195                 200                 205

Thr Gly Ser Leu Glu Pro Ser Ser Gly Ala Ser Gly Pro Gln Val Ser
    210                 215                 220

Ser Val Lys Leu Ser Thr Met Met Ser Pro Thr Thr Ser Thr Asn Ala
225                 230                 235                 240

Ser Thr Val Pro Phe Arg Asn Pro Asp Glu Asn Ser Arg Gly Met Leu
                245                 250                 255

Pro Val Ala Val Leu Val Ala Leu Leu Ala Val Ile Val Leu Val Ala
            260                 265                 270

Leu Leu Leu Leu Trp Arg Arg Arg Gln Lys Arg Arg Thr Gly Ala Leu
        275                 280                 285

Val Leu Ser Arg Gly Gly Lys Arg Asn Gly Val Val Asp Ala Trp Ala
    290                 295                 300

Gly Pro Ala Gln Val Pro Glu Glu Gly Ala Val Thr Val Thr Val Gly
305                 310                 315                 320

Gly Ser Gly Gly Asp Lys Gly Ser Gly Phe Pro Asp Gly Glu Gly Ser
                325                 330                 335
```

-continued

```
Ser Arg Arg Pro Thr Leu Thr Thr Phe Phe Gly Arg Arg Lys Ser Arg
            340             345             350

Gln Gly Ser Leu Ala Met Glu Glu Leu Lys Ser Gly Ser Gly Pro Ser
        355             360             365

Leu Lys Gly Glu Glu Glu Pro Leu Val Ala Ser Glu Asp Gly Ala Val
    370             375             380

Asp Ala Pro Ala Pro Asp Glu Pro Glu Gly Gly Asp Gly Ala Ala Pro
385             390             395             400
```

REAGENTS, METHODS, AND KITS FOR THE CLASSIFICATION OF CANCER

CROSS-REFERENCE TO RELATED APPLICATIONS

This application claims priority under 35 USC §119(e) to U.S. Provisional Patent Application 61/790,898, filed Mar. 15, 2013, and U.S. Provisional Patent Application 61/619,002, filed Apr. 2, 2012, the entireties of which are incorporated herein by reference.

STATEMENT REGARDING FEDERALLY SPONSORED RESEARCH

This invention was made with United States government support awarded by the Department of Defense Breast Cancer Research Program of the Office of the Congressionally Directed Medical Research Programs (Concept Award W81XWH-09-1-0629). The United States government has certain rights in this invention.

FIELD OF THE INVENTION

The present invention relates to reagents, methods, and kits for the classification of cancer in humans.

BACKGROUND

Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer.

If a tumor is suspected to be malignant, a doctor removes a sample of tissue or the entire tumor in a procedure called a biopsy. A pathologist examines the tissue to determine whether the tumor is benign or malignant. The pathologist can also determine the tumor grade and identify other characteristics of the tumor cells.

Based on the microscopic appearance of cancer cells, pathologists commonly describe tumor grade by four degrees of severity: Grades 1, 2, 3, and 4. The cells of Grade 1 tumors resemble normal cells, and tend to grow and multiply slowly. Grade 1 tumors are generally considered the least aggressive in behavior. At the other end of the spectrum, the cells of Grade 3 or Grade 4 tumors do not look like normal cells of the same type. Grade 3 and 4 tumors tend to grow rapidly and spread faster than tumors with a lower grade.

Doctors use tumor grade among other factors to develop an individual treatment plan for the patient and to predict the patient's prognosis. Generally, a lower grade indicates a better prognosis, such as the chance of recovery or recurrence.

However, tumor grading systems are not always straightforward. First, the grading systems are largely based on qualitative parameters, such as the morphology of the cells. Second, grading systems are often different for different types of cancer. For example, pathologists use the Gleason system to describe the degree of differentiation of prostate cancer cells. The Gleason system uses scores ranging from Grade 2 to Grade 10. Other grading systems include the Bloom-Richardson system for breast cancer and the Fuhrman system for kidney cancer.

A single, more objective classification system is needed for determining the prognosis and treatment plan for different types of cancers.

SUMMARY OF THE INVENTION

The present invention is directed to reagents, methods, and kits for the classification of cancer that comprise antibodies that bind to specific regions of CD43. The antibodies comprise antibodies that are capable of specifically binding the cytoplasmic tail of CD43 and antibodies that are capable of specifically binding the extracellular domain of CD43. An exemplary antibody capable of specifically binding the cytoplasmic tail of CD43 is a rabbit polyclonal antibody (SSGZ) that specifically binds epitopes within a 26 amino acid peptide representing the terminal portion of the C-terminal domain of human CD43. The SSGZ antibody either alone or in combination with other antibodies is able to generate a classification of human cancer and to identify and characterize cancer tissue in lung and breast tissue, among others. The cancer may therefore be treated in accordance with the characterization.

One method of the invention is a method of characterizing cancerous tissue. The method comprises contacting tissue suspected of being cancerous with a first antibody in a format capable of resolving nuclear binding and cytoplasmic binding, wherein the first antibody is an antibody capable of specifically binding cytoplasmic tail of CD43; contacting the tissue with a second antibody in the format capable of resolving nuclear binding and cytoplasmic binding, wherein the second antibody is an antibody capable of specifically binding extracellular domain of CD43; and resolving cellular localization of any binding with the first antibody and the second antibody to the tissue. Depending on the localization of any binding with the first antibody and the second antibody in the resolving step, the resolving step can distinguish cancerous tissue from non-cancerous tissue, more aggressive cancer from less aggressive cancer, and, in the case of lung cancer, small cell lung cancer (SCLC) from non-small cell lung cancer (NSCLC). The particular binding patterns of the first and second antibodies that permit such characterization of cancer tissue is described in detail below. In some versions, the characterization methods are performed on the tissue ex vivo. In some versions, the characterization methods are performed on the tissue in vivo.

In some versions, the method further comprises treating a patient providing the tissue based on the resolved cellular localization of any binding with the first antibody and the second antibody to the tissue. For example, if a tissue is characterized as an aggressive cancer as opposed to a less aggressive or non-aggressive cancer, the patient is treated for an aggressive cancer. If a tissue is characterized as a less aggressive or non-aggressive cancer as opposed to an aggressive cancer, the patient is treated for a less aggressive or non-aggressive cancer. If a tissue is characterized as probable small cell lung cancer tissue, the patient is treated with a small lung cancer cell-specific treatment. If a tissue is characterized as probable non-small cell lung cancer tissue, the patient is treated with a non-small lung cancer cell-specific treatment.

An example of a kit provided by the present invention comprises a first antibody, wherein the first antibody is capable of specifically binding cytoplasmic tail of CD43; a second antibody, wherein the second antibody is capable of specifically binding extracellular domain of CD43; and a signal-generating reagent which binds to the first antibody, the second antibody, or the first antibody and the second antibody without substantially interfering with binding of the first antibody to the cytoplasmic tail of CD43 or binding of the second antibody to the extracellular domain of CD43.

In some versions of the aforementioned methods and kits, the first antibody is capable of specifically binding at least a portion of a polypeptide consisting of sequence WRRRQKRRTGALVLSRGGKRNGV-VDAWAGPAQVPEEGAVTVTVGGSGGDKGSGF PDGEGSSRRPTLTTFFGRRK-SRQGSLAMEELKSGSGPSLKGEEEPLVASEDGAVDAP APDEPEGGDGAAP (residues 277-400 of SEQ ID NO:1).

In some versions of the aforementioned methods and kits, the first antibody is capable of specifically binding at least a portion of a polypeptide consisting of sequence PLVASEDGAVDAPAPDEPEGGDGAAP (residues 375-400 of SEQ ID NO:1).

In some versions of the aforementioned methods and kits, the second antibody is capable of specifically binding at least a portion of a polypeptide consisting of sequence STTAVQTPTSGEPLVSTSEPLSSK-MYTTSITSDPKADSTGDQTSALPPSTSINEGSPLW TSI-GASTGSPLPEPTTYQEVSIKMSSVPQET-PHATSHPAVPITANSLGSHTVTGGTITTN SPETSSRTSGAPVTTAASSLETSRGTSG-PPLTMATVSLETSKGTSGPPVTMATDSLETS TGTTGP-PVTMTTGSLEPSSGASGPQVSSVKLST-MMSPTTSTNASTVPFRNPDENSR (residues 20-253 of SEQ ID NO:1).

The objects and advantages of the invention will appear more fully from the following detailed description of the preferred embodiment of the invention made in conjunction with the accompanying drawings.

BRIEF DESCRIPTION OF THE DRAWINGS

FIG. 1 depicts an annotated sequence of an exemplary CD43 protein from which peptides may be derived to generate antibodies of the invention.

FIG. 3A-3R depict immunohistochemical staining of NSCLC, SCLC, and control lung tissue sections. FIGS. 3A-3C depict triplicate sections of 5 µm cut from formalin-fixed, paraffin-embedded tissue obtained from squamous NSCLC. FIGS. 3D-3F depict triplicate sections of adenocarcinoma NSCLC. FIGS. 3G-3I depict triplicate sections of carcinoid NSCLC. FIGS. 3J-3O depicts triplicate sections of two cases of SCLC. FIGS. 3P-3R depict triplicate sections of non-malignant lung tissue obtained from a patient with mild silicosis. FIGS. 3A, 3D, 3G, 3J, 3M, and 3P show sections stained with hematoxylin and eosin (H & E). FIGS. 3B, 3E, 3H, 3K, 3N, and 3Q show sections incubated with a non-immune rabbit IgG antibody (Caltag Laboratories, Inc., Burlingame, Calif.) (Non-Immune). FIGS. 3C, 3F, 3I, 3L, 3O, and 3R show sections incubated with the rabbit polyclonal antibody SSGZ that specifically binds CD43 (CD43-SSGZ). SSGZ binding to CD43 and background non-immune IgG binding was visualized using the EnVision™+System-HRP (Dako North America, Inc., Carpinteria, Calif.). Counterstaining with hematoxylin visualized nuclei. Grey precipitates indicate SSGZ binding to CD43. All cases of adenocarcinoma, carcinoid carcinoma and squamous cell carcinoma exhibited predominant nuclear localization of SSGZ staining. Cases of SCLC exhibited staining predominantly either in the nucleus (N) or cytoplasm (C). Arrowed are leukocytes present in non-malignant tissue that exhibit membrane staining. Bars denote lengths of 100 µm. The data in FIG. 3 show that CD43 is expressed by primary tumors of NSCLC and SCLC but not by non-malignant lung tissue.

DETAILED DESCRIPTION OF THE INVENTION

Figure 2:
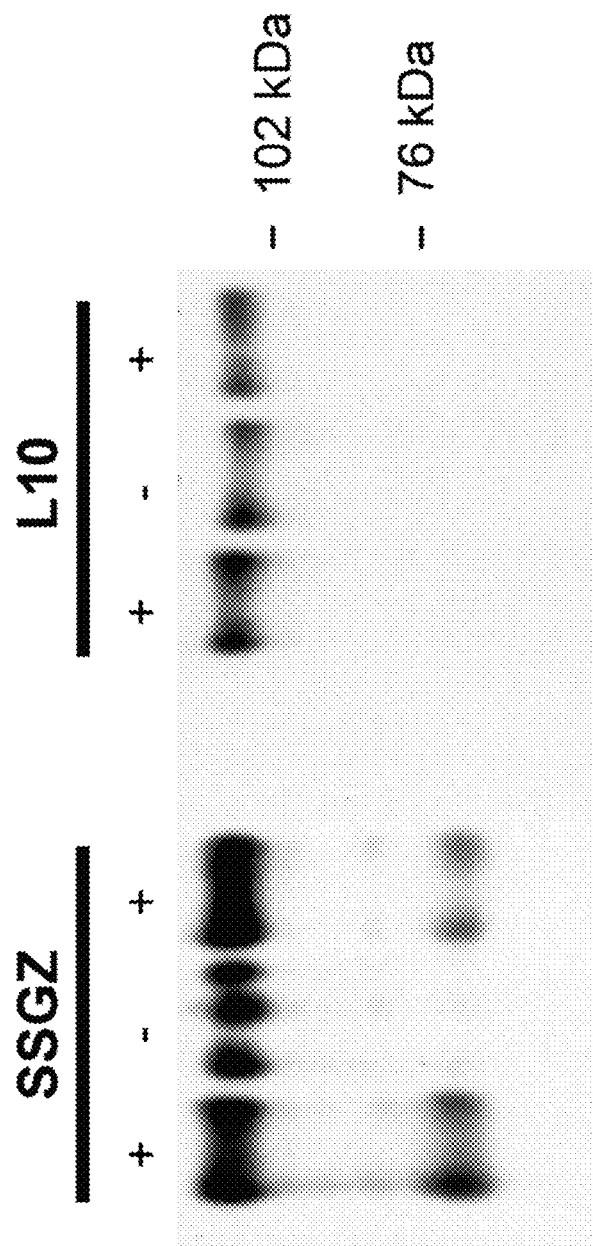
FIG. 2 depicts a Western blot of total protein lysates of Jurkat T-lymphocytic cells treated (+) or untreated (−) with 100 ng/ml of phorbol myristate acetate. Proteins are visualized with the mouse monoclonal antibody L10 and the rabbit polyclonal antibody SSGZ. The L10 antibody recognizes the extracellular domain of CD43 and detects the intact molecule of over 102 kDa. The SSGZ antibody recognizes the intracellular domain of CD43 and detects both the intact molecule and also the proteolytic fragment of under 76 kDa that is produced during leukocyte activation (Andersson et al., 2005; Mambole, et al., 2008; Seo and Ziltener, 2009)

One aspect of the present invention comprises antibodies capable of binding various, specific portions of CD43. These antibodies are useful in diagnosing cancer cells and characterizing cancer cells for directing treatment of cancer patients.

The term "antibody," as used herein, generally refers to a glycoprotein produced by B lymphocyte cells in response to exposure to an antigen that binds specifically to that antigen. In some cases, non-B lymphocyte cells, such as CHO cells or others, can be engineered to produce antibodies. An example of such cells includes the "GPEX"-brand cells produced by Catalent Pharma Solutions (Somerset, N.J.). The term "antibody" is used in its broadest sense and specifically covers monoclonal antibodies (including full length monoclonal antibodies), polyclonal antibodies, multispecific antibodies (e.g., bispecific antibodies) and antibody fragments so long as they exhibit the desired biological activity.

As used herein, the term "antibody" also includes any protein or peptide-containing molecule that comprises at least a portion of an immunoglobulin molecule, such as, but not limited to, one complementarity determining region (CDR) of a heavy chain or light chain constant region, a framework region, or any portion thereof.

The term "antibody fragment," as used herein, refers to a portion of a full length antibody, generally the antigen binding or variable domain thereof. Antibody fragments may include Fab, Fab', F(ab')2, and Fv fragments; diabodies; linear antibodies; single-chain antibody molecules; and multi-specific antibodies from antibody fragments.

The antibodies of the invention are generated by conventional means utilizing the isolated, recombinant or modified antigens of the invention or mixtures of such antigens or antigenic fragments. For example, polyclonal antibodies are generated by conventionally stimulating the immune system of a selected animal with the isolated antigen or mixture of antigenic proteins or peptides described herein, allowing the immune system to produce natural antibodies thereto, and collecting these antibodies from the animal's blood or other biological fluid. The antibodies collected from the animal are polyclonal antibodies. See the Examples for an exemplary method of producing antibodies in such a manner.

Monoclonal antibodies (MAbs) directed against the various peptides described herein may also be generated. Hybridoma cell lines expressing desirable MAbs are generated by well-known conventional techniques. Similarly desirable high titer antibodies are generated by applying known recombinant techniques to the monoclonal or polyclonal antibodies developed to these antigens. See, e.g., PCT Patent Application No. PCT/GB85/00392; British Patent Application Publication No. GB2188638A; Amit, et al., *Science,* 233:747-753 (1986); Queen, et al., *Proc. Nat'l. Acad. Sci. USA,* 86:10029-10033 (1989); PCT Patent Application No. PCT/WO9007861; Riechmann, et al., *Nature,* 332:323-327 (1988); and Huse, et al., *Science,* 246:1275-1281 (1988a).

The antigens used to generate the antibodies of the invention may be assembled as multi-antigenic complexes (see, e.g., European Patent Application 0339695, published Nov.

2, 1989) or as simple mixtures of antigenic proteins/peptides and employed to elicit high titer antibodies capable of binding the selected antigen(s).

Further contemplated by the present invention are anti-idiotype antibodies (Ab2) and anti-anti-idiotype antibodies (Ab3). Ab2 are specific for the binding domain of the antibodies (Ab1) that bind to the antigens of the invention, and Ab3 are similar to Ab1 in their binding specificities and biological activities (see, e.g., M. Wettendorff, et al., "Modulation of anti-tumor immunity by anti-idiotypic antibodies" In Idiotypic Network and Diseases, ed. by J. Cerny and J. Hiernaux J, *Am. Soc. Microbiol*, Washington D.C.: pp. 203-229, (1990)). These anti-idiotype and anti-anti-idiotype antibodies are produced using techniques well known to those of skill in the art. Such anti-idiotype antibodies (Ab2) can bear the internal image of the antigens and are thus useful for the same purposes as the peptides described herein. In general, polyclonal antisera, monoclonal antibodies and other antibodies which bind to the selected antigen (Ab1) are useful to identify epitopes of the peptide antigen and to separate these peptides and proteins from contaminants in tissue (e.g., in chromatographic columns and the like) and in general as research tools and as starting materials essential for the development of other types of antibodies described above. Anti-idiotype antibodies (Ab2) thus may be used in place of the original antigen.

The terms "specifically bind(s)" or "specific for" means that an antigen of the present invention recognizes and binds to a first antigen, e.g., the CD43 cytoplasmic tail, with greater affinity than to other, non-specific antigens. A non-specific antigen is an antigen that shares no common epitope with the first antigen. For example, an antibody raised against a first antigen (e.g., a polypeptide) to which it binds more efficiently than to a non-specific antigen can be described as specifically binding to the first antigen. Specific binding can be tested using, for example, an enzyme-linked immunosorbant assay (ELISA), a radioimmunoassay (RIA), or a western blot assay using methodology well known in the art. In some versions of the invention, an antibody that is capable of specifically binding the cytoplasmic tail of CD43 does not substantially bind the extracellular domain of CD43 and/or other non-specific antigens. In some versions of the invention, an antibody that is capable of specifically binding the extracellular domain of CD43 does not substantially bind the cytoplasmic tail of CD43 and/or other non-specific antigens.

The antigens used to generate the antibodies of the invention may be derived from various portions of CD43. An exemplary CD43 protein from which such peptides may be derived has the sequence of GenBank Acc. No. NP_003114 (SEQ ID NO:1), an annotated version of which is shown in FIG. 1. The exemplary CD43 protein represented by SEQ ID NO:1 has the following domains:

Residues 1-400: Precursor protein;
Residues 1-19: Signal peptide;
Residues 20-400: Mature peptide;
Residues 20-253: Extracellular domain;
Residues 254-276: Transmembrane region;
Residues 277-400: Cytoplasmic tail; and
Residues 375-400: Exemplary peptide sequence used to generate the SSGZ antibody.

Some antibodies of the invention are capable of specifically binding the cytoplasmic tail of CD43. Peptides having a sequence corresponding to residues 277-400 of SEQ ID NO:1 (shown in FIG. 1 in bold) or fragments thereof can be used to generate antibodies capable of specifically binding the cytoplasmic tail of CD43. Accordingly, the antibodies generated in this manner are capable of specifically binding at least a portion of a polypeptide having a sequence corresponding to residues 277-400 of SEQ ID NO:1 or fragments thereof, such as a polypeptide consisting of residues 277-400 of SEQ ID NO: 1. Peptides having a sequence corresponding to residues 375-400 of SEQ ID NO:1 or fragments thereof can also be used to generate antibodies capable of specifically binding the cytoplasmic tail of CD43. Accordingly, antibodies generated in this manner are capable of specifically binding at least a portion of a polypeptide having a sequence corresponding to residues 375-400 of SEQ ID NO:1 (shown in FIG. 1 in bold underline), such as a polypeptide consisting of residues 375-400 of SEQ ID NO:1. An exemplary version of an antibody capable of specifically binding at least a portion of a polypeptide having a sequence corresponding to residues 375-400 of SEQ ID NO:1 is the SSGZ antibody. The generation of the SSGZ antibody and its binding properties are described in further detail below. Other antibodies that are capable of specifically binding the cytoplasmic tail of CD43 include 3A1, 1E12, 1C5, 2C2, 1B6, 6B11, 1D12, 4D2, 6B12, and 3E12 as described by Sikut et al. *Int J. Cancer.* 1999; 82:52-8.

Other antibodies of the invention are capable of specifically binding the extracellular domain of CD43. Peptides having a sequence corresponding to residues 20-253 of SEQ ID NO:1 (shown in FIG. 1 as underlined) or fragments thereof can be used to generate the antibodies. The peptides are preferably generated in cells, such as mammalian cells, capable of glycosylating the peptide. The antibodies generated with peptides having a sequence corresponding to residues 20-253 of SEQ ID NO:1 or fragments thereof are capable of specifically binding at least portion of a polypeptide having a sequence corresponding to residues 20-253 of SEQ ID NO:1, such as a polypeptide consisting of residues 20-253 of SEQ ID NO:1. An exemplary antibody capable of specifically binding the CD43 cytoplasmic domain includes the L10 antibody as described by Remold-O'Donnell et al. *J Exp Med.* 1984; 159:1705-23.

The antibodies described herein can be used in methods of characterizing cancerous tissue. The antibodies can be used to characterize any type of cancer in any type of tissue. Exemplary cancers include lung and breast cancer. Other applicable cancers include bladder, prostate, testes, kidney, thyroid, larynx, stomach, colon, adenoid cystic, gynecological, and brain cancers, other nonhematopoietic cancers (see Santamaria et al., *Cancer Research* 56, 3326-3529, Aug. 1, 1996), and others.

An exemplary method of characterizing cancerous tissue comprises contacting the tissue with an antibody capable of specifically binding the cytoplasmic tail of CD43, contacting the tissue with an antibody capable of specifically binding the extracellular domain of CD43, and resolving the cellular localization of any binding of the antibody capable of specifically binding the cytoplasmic tail of CD43 and the antibody capable of specifically binding the extracellular domain of CD43.

The tissue may comprise one or more cells or groups of cells taken from a tissue suspected of being cancerous, including lung, breast, bladder, prostate, testes, kidney, thyroid, larynx, stomach tissues, colon, brain, and vaginal tissues, among others. Any methods for obtaining tissues through biopsy are acceptable. In some versions of the invention, cells are obtained then dispersed, proliferated in culture, and potentially processed before being subjected to the contacting and resolving steps. In other versions of the invention, whole pieces of connected groups of cells, i.e., sections, etc., are excised and either fixed or otherwise processed before being subjected to the contacting and resolving steps. As used herein, "tissue" refers at least to individual intact cells; groups of intact individual cells; groups of intact, connected cells; lysates of cells; fractionated lysates of cells; isolated cellular proteins; and other processed biological matter from cancerous or potentially cancerous tumors.

The steps of contacting the tissue with an antibody capable of specifically binding the cytoplasmic tail of CD43 and contacting the tissue with an antibody capable of specifically binding the extracellular domain of CD43 may be performed on the same portion of the tissue or a different portion of the tissue. For example, the contacting with the antibody capable of specifically binding the cytoplasmic tail of CD43 and the contacting with the antibody capable of specifically binding the extracellular domain of CD43 may be performed on a single cell, a single group of cells, or a single portion of lysate from cells obtained from a tumor. If the contacting is performed on a different portion of the tissue, the different portions of the tissue should be obtained from the same tumor and preferably proximal areas of the tumor so that the binding of the antibodies in each portion is representative of the other portion and, preferably, of the tumor as a whole.

The antibody contacting steps are preferably performed in a format capable of resolving nuclear binding and cytoplasmic binding. A format capable of resolving nuclear binding and cytoplasmic binding is one that permits determining whether the antibody binds to nuclear cellular components and not cytoplasmic cellular components, cytoplasmic cellular components and not nuclear components, or both nuclear and cytoplasmic cellular components. "Nuclear components," refer to components that reside in the nucleus in the intact cell. "Cytoplasmic components" refer to components that reside in the cytoplasm in the intact cell, i.e., outside the nucleus but inside the plasma membrane. Accordingly, the terms "nuclear binding" and "cytoplasmic binding" refer to binding of the antibodies to nuclear components or cytoplasmic components whether or not such components currently reside in the nucleus or the cytoplasm, respectively, at the time of the contacting. Suitable formats that may be capable of resolving nuclear binding and cytoplasmic binding may include immunocytochemistry, immunohistochemistry, immunoblotting, and enzyme-linked immunosorbent assay (ELISA), among others, depending on certain upstream and downstream procedures as discussed in further detail below.

The step of resolving the cellular localization of any binding of the antibody capable of specifically binding the cytoplasmic tail of CD43 and the antibody capable of specifically binding the extracellular domain of CD43 can be performed by detecting a detectable signal from a label bound or conjugated either to the antibody itself or to another molecule that specifically binds, either directly or indirectly, to the antibody. The label or the molecule to which the label is bound or conjugated is referred to herein as a "signal-generating reagent." The signal-generating reagent preferably binds specifically to an antibody of the invention without substantially interfering with binding of the antibody. A non-limiting example of a signal-generating reagent is a labeled secondary antibody that specifically binds to an antibody of the invention.

The labels are capable, alone or in concert with other compositions or compounds, of providing a detectable signal. The label is detectable visually, e.g., colorimetrically, or by other known methods. A variety of enzyme systems have been described in the art which will operate to reveal a colorimetric signal in an assay. As one example, glucose oxidase (which uses glucose as a substrate) releases peroxide as a product. Peroxidase, which reacts with peroxide and a hydrogen donor such as tetramethyl benzidine (TMB), produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength. Other label systems that may be utilized in the methods of this invention are detectable by other means, e.g., colored latex microparticles (Bangs Laboratories, Ind.) in which a dye is embedded may be used in place of enzymes to form conjugates with the antibodies and provide a visual signal indicative of the presence of the resulting complex in applicable assays. Still other labels include fluorescent compounds, radioactive compounds or elements. Detectable labels for attachment to antibodies useful in diagnostic assays of this invention may be easily selected from among numerous compositions known and readily available to one skilled in the art of diagnostic assays. The methods and antibodies of this invention are not limited by the particular detectable label or label system employed.

The step of resolving the cellular localization of any binding of the antibody capable of specifically binding the cytoplasmic tail of CD43 and the antibody capable of specifically binding the extracellular domain of CD43 can further be performed by any of a number of methods. In immunocytochemistry and immunohistochemistry, cellular localization can be determined by colocalization of the signal from antibody binding with known organelle or cell-localization markers, as typically determined through microscopy. Nuclear, cell-surface, and other cell localization markers are well known in the art. For example, 4',6-diamidino-2-phenylindole (DAPI) is a commonly used nuclear marker, and the low-density lipoprotein receptor (LDLR) is a commonly used cell-surface marker. Cellular localization can also be determined by visual inspection. Nuclear binding is typically revealed in the form of a distinct, non-hollow circular shape in an internal portion of a cell. Cell-surface binding is typically revealed in the form of a distinct, hollow, continuous circular shape defining the periphery of a cell. Intracellular or cytoplasmic binding is typically revealed by diffuse staining within the bounds of the periphery of a cell. Hematoxylin and eosin (H&E) staining can be performed on the tissue for comparison purposes to resolve the nucleus from other cellular structures. Various software programs can be used to detect and quantitate the cellular localization of a signal. An example of such a program is METAMORPH-brand microscopy automation and image analysis software (Molecular Devices, Inc., Sunnyvale, Calif.). The immunocytochemistry or immunohistochemistry can be used either on dispersed cells or whole tissue sections. The term "immunocytochemistry" typically refers in the art to immunostaining dispersed cells. The term "immunohistochemistry" typically refers in the art to immunostaining tissue sections.

The step of resolving the cellular localization of any binding of the antibody capable of specifically binding the cytoplasmic tail of CD43 and the antibody capable of specifically binding the extracellular domain of CD43 can also be performed through immunoblotting, enzyme-linked immunosorbent assay (ELISA), or other methods with subcellularly fractionated tissue lysates. Methods for performing subcellular fractionation of lysates into nuclear, membrane, cytoplasmic components are well-known in the art. In addition, many kits are commercially available for performing such fractionation methods. One example of such a kit is the Subcellular Protein Fractionation Kit from Thermo Fisher Scientific (Rockford, Ill.). Detection of antibody binding to components in one or more subcellular fractions effectively indicates the cellular localization of antibody binding. Accordingly, some versions of the invention comprise subcellularly fractionating tissue lysates into nuclear, membrane, and cytoplasmic components, contacting each fraction with a first antibody which is capable of specifically binding the cytoplasmic tail of CD43 and a second antibody which is capable of specifically binding the extracellular domain of CD43, and resolving the cellular localization of any binding of the first antibody and the second antibody by determining which fractions the first and second antibodies either bind or do not bind.

As used herein, "intracellular" localization or binding refers to localization or binding occurring internally with respect to a cell's plasma membrane or cell surface and may include cytoplasmic and/or nuclear localization or binding. "Cell surface" localization or binding refers to localization or binding occurring on the periphery of the cell, such as on the plasma membrane. "Nuclear" localization or binding refers to localization or binding occurring on or within the nucleus of the cell. "Cytoplasmic" localization or binding refers to non-nuclear intracellular localization or binding.

As outlined in the examples, the invention provides methods for identifying and characterizing cancer tissue by resolving the cellular localization of binding of particular antibodies.

In some versions, intracellular binding of an antibody capable of specifically binding the cytoplasmic tail of CD43 indicates that a cell is a cancer cell. In some versions, nuclear binding of an antibody capable of specifically binding the cytoplasmic tail of CD43 identifies the cell as a cancer cell.

In some versions, nuclear binding with an antibody capable of specifically binding the cytoplasmic tail of CD43, a lack of cytoplasmic binding with the antibody capable of specifically binding the cytoplasmic tail of CD43, a lack of nuclear binding with an antibody capable of specifically binding the extracellular domain of CD43, and a lack of cytoplasmic binding with the antibody capable of specifically binding the extracellular domain of CD43 characterizes the tissue as being or comprising an aggressive cancer and, specifically, as being more aggressively cancerous than tissue not showing nuclear binding with the antibody capable of specifically binding the cytoplasmic tail of CD43, a lack of cytoplasmic binding with the antibody capable of specifically binding the cytoplasmic tail of CD43, a lack of nuclear binding with the antibody capable of specifically binding the extracellular domain of CD43, and a lack of cytoplasmic binding with the antibody capable of specifically binding the extracellular domain of CD43.

In some versions, nuclear binding with an antibody capable of specifically binding the cytoplasmic tail of CD43, a lack of cytoplasmic binding with the antibody capable of specifically binding the cytoplasmic tail of CD43, a lack of nuclear binding with an antibody capable of specifically binding the extracellular domain of CD43, and a lack of cytoplasmic binding with the antibody capable of specifically binding the extracellular domain of CD43 indicates decreased rates of survival of a patient providing the tissue compared to survival of a patient providing tissue characterized by nuclear binding with the antibody capable of specifically binding the cytoplasmic tail of CD43 and at least cytoplasmic binding with the antibody capable of specifically binding the extracellular domain of CD43. "At least cytoplasmic binding with the antibody capable of specifically binding the extracellular domain of CD43" also means that the antibody capable of specifically binding the extracellular domain of CD43 may also show nuclear binding.

In some versions, nuclear binding with an antibody capable of specifically binding the cytoplasmic tail of CD43, a lack of cytoplasmic binding with the antibody capable of specifically binding the cytoplasmic tail of CD43, a lack of nuclear binding with an antibody capable of specifically binding the extracellular domain of CD43, and a lack of cytoplasmic binding with the antibody capable of specifically binding the extracellular domain of CD43 indicates decreased rates of survival of a patient providing the tissue compared to survival of a patient providing tissue characterized by nuclear binding with the antibody capable of specifically binding the cytoplasmic tail of CD43, cytoplasmic binding with the antibody capable of specifically binding the extracellular domain of CD43, and nuclear binding with the antibody capable of specifically binding the extracellular domain of CD43.

In some versions, nuclear binding with an antibody capable of specifically binding the cytoplasmic tail of CD43, a lack of cytoplasmic binding with the antibody capable of specifically binding the cytoplasmic tail of CD43, cytoplasmic binding with an antibody capable of specifically binding the extracellular domain of CD43, and a lack of nuclear binding with the antibody capable of specifically binding the extracellular domain of CD43 indicates decreased rates of survival of a patient providing the tissue compared to survival of a patient providing tissue characterized by nuclear binding with the antibody capable of specifically binding the cytoplasmic tail of CD43, cytoplasmic binding with the antibody capable of specifically binding the extracellular domain of CD43, and nuclear binding with the antibody capable of specifically binding the extracellular domain of CD43.

In some versions, the tissue is lung tissue. Nuclear binding to the lung tissue with an antibody capable of specifically binding the cytoplasmic tail of CD43, a lack of cytoplasmic binding with an antibody capable of specifically binding the cytoplasmic tail of CD43, a lack of nuclear binding with an antibody capable of specifically binding the extracellular domain of CD43, and a lack of cytoplasmic binding with the antibody capable of specifically binding the extracellular domain of CD43 characterizes the tissue as probable small cell lung cancer tissue.

In some versions, cytoplasmic binding to lung tissue with an antibody capable of specifically binding the extracellular domain of CD43 characterizes the tissue as probable non-small cell lung cancer tissue. This may be the case whether or not the antibody capable of specifically binding the extracellular domain of CD43 also shows nuclear binding and whether or not an antibody capable of specifically binding the cytoplasmic tail of CD43 shows nuclear binding.

In some versions, nuclear binding to lung tissue with an antibody capable of specifically binding the cytoplasmic tail of CD43 and cytoplasmic binding with an antibody capable of specifically binding the extracellular domain of CD43 characterizes the tissue as probable non-small cell lung cancer tissue. This may be the case whether or not the antibody capable of specifically binding the extracellular domain of CD43 also shows nuclear binding.

In some versions, nuclear binding to lung tissue with an antibody capable of specifically binding the cytoplasmic tail of CD43, cytoplasmic binding with an antibody capable of specifically binding the extracellular domain of CD43, and nuclear binding with the antibody capable of specifically binding the extracellular domain of CD43 characterizes the tissue as probable non-small cell lung cancer tissue.

As used herein with respect to assessment of binding to a single cell, "binding" refers to the presence of a localized signal substantially the same as a suitable positive control and/or substantially greater than a suitable negative control. "Lack of binding" refers to a localized signal substantially less than a suitable positive control and/or substantially the same as a suitable negative control. As used herein with respect to assessment of binding to a population of cells, "binding" refers to detection of a localized signal that is substantially the same as a suitable positive control and/or substantially greater than a suitable negative control in 10% or more of cells. "Lack of binding" refers to detection of a localized signal that is substantially less than a suitable positive control and/or substantially the same as a suitable negative control in less than 10% of cells. "Probable" used with reference to "probable non-small cell cancer tissue," "probable small cell cancer tissue," and the like means that the tissue is statistically more likely than not a cancer tissue of the specified type.

The present invention is not limited to identifying cancer cells by detecting and resolving the intracellular localization of particular portions of CD43 with the antibodies herein described. The invention includes detecting and resolving the intracellular localization of a peptide comprising the CD43 cytoplasmic tail (residues 277-400 of SEQ ID NO:1 or others) or fragments thereof (residues 375-400 of SEQ ID NO:1 or others) by any method. The invention may additionally include detecting and resolving the intracellular localization of a peptide comprising the extracellular domain of CD43 (residues 20-253 of SEQ ID NO:1) or fragments thereof by any method. The practical import of such detecting for the purpose of identifying and characterizing cancer cells is apparent from discussions elsewhere in the present description of the invention.

Some versions of the invention include obtaining tissue from a patient suspected of having cancer, identifying cancerous tissue according to the methods described herein to confirm presence of cancer in a patient, and treating the confirmed cancer in the patient. For treating cancers generally, any known cancer treatment known in the art is acceptable. Examples include surgery, chemotherapy, and/or radiation.

Some versions of the invention comprise treating a patient based on the resolved cellular localization of the binding with the antibody capable of specifically binding the cytoplasmic tail of CD43 and the antibody capable of specifically binding the extracellular domain of CD43. For example, if the antibody capable of specifically binding the cytoplasmic tail of CD43 shows nuclear binding and a lack of cytoplasmic binding and the antibody capable of specifically binding the extracellular domain of CD43 shows a lack of nuclear binding and a lack of cytoplasmic binding, the tissue is characterized as an aggressive cancer as opposed to a less-aggressive or a non-aggressive cancer. Such an aggressive cancer is preferably treated with a combination of surgical removal of the tumor, chemotherapy, radiation therapy, and/or antibody therapy. Some preferred treatments include at least surgical removal of the tumor, chemotherapy, and radiation therapy. Other preferred treatments include radiation therapy and chemotherapy. Other preferred treatments include surgical removal of the tumor and chemotherapy. Other preferred treatments include surgical removal of the tumor and radiation therapy. Other preferred treatments include surgical removal of the tumor, chemotherapy, radiation therapy, and antibody therapy. In some cases, such characterized cancers are breast cancers.

If the antibody capable of specifically binding the cytoplasmic tail of CD43 shows nuclear binding and a lack of cytoplasmic binding and the antibody capable of specifically binding the extracellular domain of CD43 shows nuclear binding and cytoplasmic binding, the tissue is characterized as a less-aggressive or a non-aggressive cancer as opposed to an aggressive cancer. Such a less-aggressive or non-aggressive cancer is preferably treated with fewer than all of surgical removal of the tumor, chemotherapy, radiation therapy, and antibody therapy. Examples include only surgical removal of the tumor, only chemotherapy, only radiation therapy, or only antibody therapy. In some cases, such characterized cancers are breast cancers.

Some versions of the invention include identifying cancerous tissue in a patient as either non-small cell lung cancer (NSCLC) or small cell lung cancer (SCLC) by the methods described herein and then treating a patient from whom such cells were derived with either a NSCLC-specific treatment or a SCLC-specific treatment, respectively. SCLC is considered to be distinct from NSCLCs because of its clinical and biologic characteristics. Small cell lung cancer exhibits aggressive behavior with rapid growth, early spread to distant sites, and frequent association with distinct paraneoplastic syndromes. Treatment regimens for SCLC differ than those for NSCLCs. SCLC is exquisitely sensitive to chemotherapy and radiation therapy. Accordingly, treatment of SCLC involves combination chemotherapy, usually with a platinum-containing regimen, and thoracic radiation therapy. If the patient achieves a complete remission, he or she is typically offered prophylactic cranial irradiation. Surgery plays little, if any, role in the treatment of SCLC. By contrast, surgical resection remains the mainstay of treatment for all patients with NSCLC. The methods of identifying SCLC cells and NSCLC cells described herein can identify the specific types of cancers present in patients and thereby indicate the appropriate treatment regimens described above (i.e., NSCLC-specific or SCLC-specific treatments).

The invention further includes kits for performing any of the methods described herein. The kit can contain any reagent, antibody, or element described herein that can be used for performing any of the methods described herein. One exemplary version is a kit that includes a first antibody which is capable of specifically binding the cytoplasmic tail of CD43, a second antibody which is capable of specifically binding the extracellular domain of CD43, and one or more signal-generating reagents which specifically bind to the first and/or second antibodies without substantially interfering with binding of the first or second antibodies to the cytoplasmic tail or extracellular domain, respectively, of CD43. In some versions, the kit contains at least one signal-generating reagent that specifically binds to the first antibody such that it does not substantially bind to the second antibody. In some versions, the kit contains at least one signal-generating reagent the specifically binds to the second antibody such that it does not substantially bind to the first antibody. Alternative or additional elements are acceptable for inclusion in the kits of the invention.

The elements and method steps described herein can be used in any combination whether explicitly described or not. All combinations of method steps as described herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Under normal circumstances CD43, which has also been called large sialoglycoprotein, gpL115, leukosialin and sialophorin, is only expressed on the surface of leukocytes and platelets [1, 2]. The mature CD43 molecule is composed of 381 amino acids divided between a 235 residue extracellular region, a 23 residue transmembrane region and a 123 amino acid C-terminal intracellular region [3, 4]. The extracellular region contains approximately 84 sialylated O-linked carbohydrate units and appears by electron microscopy to be a rod-like structure extending 45 nm from the cell surface [5].

CD43 has been described as a Janus molecule after the Roman god with two faces [1]. This analogy reflects the finding that CD43 can perform diametrically opposite functions. First, depending upon how it is engaged at the cell surface, CD43 can either induce or protect against leukocyte apoptosis [6-10]. Second, depending upon the status of leukocyte activation, CD43 can act either as an anti-adhesion barrier molecule or a pro-adhesion receptor [6, 11-18].

While leukocytes are at rest, the length, bulk, abundance and strong negative charge of CD43 combine to inhibit adhesion and maintain leukocytes in the circulation [11-14]. During leukocyte activation, the surface expression of CD43 is reduced both by repression of the gene by which it is encoded and also by proteolytic cleavage of its extracellular domain [19-25]. In addition, CD43 is excluded from foci of cell-cell contact and accumulates at the contracting uropod during polarization [13, 26-29]. Together, this down-regulation and redistribution facilitate intercellular interaction and migration, effected by other leukocyte molecules such as the β2 integrins [26]. In addition to mitigation of its anti-adhesive function, CD43 also plays a positive role in the performance of activated leukocytes. Changes in the glycosylation pattern of its extracellular domain allow CD43 to function as a pro-adhesive counter receptor for galectin-1, ICAM-1, E-selectin, sialoadhesin and MHC class I molecules [6, 13, 15-18, 28, 30, 31].

While CD43 is normally restricted in its expression to leukocytes and platelets, aberrant expression has been described in colon and salivary gland cancers [32-35]. In addition, limited analysis suggested that lung, breast, bladder, prostate, testes, kidney, thyroid, larynx and stomach cancers might also be characterized by CD43 expression [36, 37].

A significant concern with previous studies of CD43 expression in cancer is that they used monoclonal antibodies recognizing extracellular domains of CD43 as it is expressed by leukocytes. The extracellular domain of CD43 is heavily and variably glycosylated [1]. Consequently, antibodies raised against the extracellular domain of leukocyte CD43 are likely prone to give false negative evaluations of CD43 as it is expressed by cancer cells. This is an important consideration given that based on only two cases of SCLC one previous report concluded that CD43 is expressed by NSCLC but not by SCLC [36].

Numerous gene expression profiles have been compiled for lung cancer [38]. However, none has identified CD43 as being aberrantly expressed. This highlights an intrinsic limitation of the DNA microarray technique since any abnormal CD43 expression in lung cancer would appear to be due to the abnormal induction of translation and/or protein stability as opposed to induced mRNA stability and/or transcription.

The following examples describe aspects of an antibody-based cancer-characterization test that detects the presence and localization of CD43 in the identification and characterization of cancer cells for the appropriate treatment of cancer.

Example 1

Generation of the Polyclonal Antibody SSGZ

Due to concerns about the antibodies used in previous studies of CD43 expression in cancer cells, we raised a rabbit polyclonal antibody against the terminal 26 amino acids of its intracellular domain. This antibody was named "SSGZ."

Covalab S.A.S. (Villeurbanne, France) synthesized a peptide of 26 amino acids with the sequence $NH_2$-PLVASEDGAVDAPAPDEPEGGDGAAP-COOH. This peptide corresponds to residues 375-400 of the primary translation product of CD43 mRNA [3, 4]. These residues are the 26 terminal residues of the intracellular domain of CD43. The same company then used glutaraldehyde cross-linking to conjugate the N-terminus of the peptide to keyhole limpet hemocyanin. Next, 0.5 ml containing 100 µg of the conjugated peptide was mixed with 0.5 ml of Complete Freund Adjuvant, and this was then injected intradermally into a New Zealand White rabbit. After 21 days and then again after 42 days intradermal injection was repeated but with Incomplete Freund Adjuvant. After 63 days and then again at 91 days subcutaneous injection was performed with Incomplete Freund Adjuvant. After 116 days serum was drawn and IgG was immunopurified.

Example 2

Verification of CD43 Binding by SSGZ

SSGZ was tested for CD43 binding using western blot analysis. SSGZ detected a single major protein in extracts of Jurkat T-lymphocytic cells that had an electrophoretic mobility corresponding to the major protein detected by the monoclonal antibody L10 (FIG. 2). The L10 antibody binds the N terminus of CD43 [40].

Example 3

Immunocytochemistry

Formalin-fixed paraffin-embedded blocks containing human lung or breast tissue were serially sectioned at 4 µm and dried overnight on Colorfrost® Plus microscope slides (Thermo Fisher Scientific, Inc., Waltham, Mass.). Next, sample slides were deparaffinized by a 60 minute incubation at 60° C. followed by 4 changes of xylene, 3 changes of 100% ethanol, 2 changes of 95% ethanol and storage in tap water. One slide from each block was stained with Hematoxylin and Eosin Y. The remaining slides were subjected to a 20 minute incubation at 90-100° C. in the presence of Epitope Retrieval Solution, pH 9 (Dako North America, Inc., Carpinteria, Calif.). Next, the slides were rocked for 5 minutes at room temperature with tissue covered by the Peroxidase Blocking reagent of the EnVision+System-HRP (DAB) (Dako North America, Inc.). A rocking incubation was then performed at room temperature for 30 minutes with Surfact-Amps® X-100 (Thermo Scientific, Inc., Waltham, Mass.). One slide from each block was rocked for 45 minutes at room temperature with either an IgG non-immune rabbit or mouse antibody diluted as recommended by the manufacturer (Epitomics, Inc., Burlingame, Calif.). One slide from each block was identically incubated with either a 1:2400 dilution of the rabbit polyclonal antibody SSGZ or a 1:100 dilution of the mouse monoclonal antibody L10 [40] that specifically recognize the C and N termini of CD43, respectively. Serial rocking incubations were next performed at room temperature for 30 minutes with Labeled Polymer-HRP Anti-Rabbit or Anti-Mouse, twice for 5 minutes with Wash Buffer and 5 minutes with DAB+Chromogen (Dako North America, Inc.). Counterstaining was accomplished by dipping the slides in Hematoxylin, rinsing with tap water, dipping in 1% glacial acetic acid, rinsing again in tap water and then dipping in 1% ammonium hydroxide. Rinsing in 100% ethanol then xylene dehydrated the tissue that was finally protected by glass coverslips mounted with Permount® (Thermo Fisher Scientific, Inc.). The extent of L10 and SSGZ staining specific to the nucleus and cytoplasm was scored as either 0 or 1+. A pathologist (JJA) certified by the American Board of Pathology scored the staining in the lung cancer studies. A score of 0 indicated that staining was observed in less than 10% of the malignant material. A score of 1+ indicated that 10-70%+ of the tumor was stained.

Example 4

Characterization of Cancer in Lung Tissue as SCLC or NSCLC

A retrospective search of the files of the Gundersen Medical Foundation BioBank and the Department of Pathology at Gundersen Lutheran Medical Center identified 25 cases of SCLC dating between 1984 and 1986, 28 cases of carcinoid NSCLC dating between 1984 and 2008, 18 cases of squamous NSCLC dating between 1983 and 1984, and 20 cases of NSCLC diagnosed between 1983 and 1985 as adenocarcinoma. Also identified was one case of mild lung silicosis diagnosed in 1985. Paraffin-embedded formalin-fixed tissue representing the silicosis control case and the primary tumor of each cancer case was sectioned, stained with hematoxylin and eosin and the histological diagnosis was verified. All file searches and subsequent experimental procedures were approved by the Human Subjects Committee of Gundersen Clinic, Ltd. of La Crosse, Wis.

The SSGZ and L10 antibodies were then used to analyze the formalin-fixed paraffin-embedded primary lung tumors removed from the 25 patients with SCLC, the 28 patients with carcinoid NSCLC, the 18 patients with squamous NSCLC, and the 20 patients with NSCLC of the adenocarcinoma histological type (FIG. 3). The formalin-fixed paraffin-embedded lung tissue removed from the 52 year-old male with mild silicosis was used as a non-malignant control.

Tumors were categorized into the following 9 groups as defined by their pattern of L10 and SSGZ staining in the nucleus and cytoplasm (see Table 1):

LC/SC: Tumors exhibiting a L10 staining score of 0 in the nucleus but 1+ in the cytoplasm together with a SSGZ staining score of 0 in the nucleus and 1+ in the cytoplasm.

LC/SN: Tumors exhibiting a L10 staining score of 0 in the nucleus but 1+ in the cytoplasm together with a SSGZ staining score of 1+ in the nucleus and 0 in the cytoplasm.

LCN/SN: Tumors exhibiting a L10 staining score of 1+ in both the nucleus and cytoplasm together with a SSGZ staining score of 1+ in the nucleus and 0 in the cytoplasm.

LC: Tumors exhibiting a L10 staining score of 0 in the nucleus and 1+ in the cytoplasm together with a SSGZ staining score of 0 both in nucleus and cytoplasm.

LN: Tumors exhibiting a L10 staining score of 1+ in the nucleus and 0 in the cytoplasm together with a SSGZ staining score of 0 both in nucleus and cytoplasm.

LCN: Tumors exhibiting a L10 staining score of 1+ in both the nucleus and cytoplasm together with a SSGZ staining score of 0 both in nucleus and cytoplasm.

SN: Tumors exhibiting a L10 staining score of 0 in both the nucleus and cytoplasm together with a SSGZ staining score of 1+ in the nucleus but 0 in the cytoplasm.

SCN: Tumors exhibiting a L10 staining score of 0 in both the nucleus and cytoplasm together with a SSGZ staining score of 1+ in both the nucleus and cytoplasm.

4NG: Tumors exhibiting a L10 staining score of 0 in both the nucleus and cytoplasm together with a SSGZ staining score of 0 both in the nucleus and cytoplasm.

TABLE 1

Molecular classification of lung cancer based on intracellular patterns of CD43 expression defined by combinations of SSGZ and L10 antibody staining.

| Histologic Subtype | Total Cases | LCSC | LCSN | LCNSN | LC | LN | LCN | SN | SCN | 4NG |
|---|---|---|---|---|---|---|---|---|---|---|
| Adenocarcinoma | 20 | 0 | 7 | 2 | 6 | 0 | 0 | 4 | 1 | 0 |
| Carcinoid | 28 | 0 | 16 | 2 | 8 | 0 | 1 | 1 | 0 | 0 |
| Squamous | 18 | 0 | 9 | 2 | 3 | 0 | 0 | 2 | 0 | 2 |
| Small Cell | 25 | 1 | 2 | 0 | 3 | 1 | 0 | 16 | 0 | 2 |

No immunohistochemical signal was detected in the non-malignant control tissue except on the plasma membrane of leukocytes as would be expected for CD43 that is normally expressed. However, in SCLC, carcinoid NSCLC, squamous NSCLC and adenocarcinoma at least 10% of the malignant tissue was CD43-positive in 92%, 100%, 89% and 100% of the cases, respectively (Table 1). On the basis of distinct patterns of L10 and SSGZ staining, lung cancer can be divided into the 9 molecular categories shown in Table 1. See also Fu et al. *International Journal of Cancer,* 2013, 132: 1761-1770, incorporated herein by reference in its entirety, for additional exemplary results.

These results show that CD43 expression is a robust biomarker not only for NSCLC but also for SCLC. The discrepancy between our finding that SCLC is predominantly CD43- positive and a previous report of SCLC to be CD43-negative [36] likely stems from the different number of cases analyzed in the two studies and the use of different antibodies.

A striking feature of CD43 expression both in NSCLC and SCLC is that it is exclusively intracellular with no plasma membrane localization characteristic of leukocytes. The implication of this result is that the trafficking of CD43 in lung cancer is distinct from that in leukocytes. Another striking feature of the expression of CD43 in lung cancer is that in 85% of cases the C-terminal epitopes recognized by SSGZ are expressed exclusively in the nucleus while the N-terminal epitopes recognized by another anti-CD43 antibody L10 are localized exclusively in the cytoplasm. This segregation of the C and N termini of CD43 to different intracellular compartments implies a proteolytic cleavage event that produces a C-terminal fragment containing the nuclear localization signal of the molecule and an N-terminal fragment with this signal missing [39].

While NSCLC and SCLC are approximately equal in terms of the frequency of CD43 expression, they are quite distinct in terms of how this expression is exhibited. In NSCLC 48% of cases show C-terminal expression in the nucleus together with N-terminal expression in the cytoplasm. This molecular category of lung cancer we designated LC/SN signifying L10 expression in the cytoplasm and SSGZ staining in the nucleus. In SCLC 64% of cases also show C-terminal expression in the nucleus but expression of the N-terminus as detected by L10 is absent. This molecular category we designated SN. We predict that the differential aggressiveness of NSCLC and SCLC is related to their bias towards different molecular categories defined by CD43.

On the basis of L10 and SSGZ staining, 52% of NSCLC cases can be classified into 6 groups other than LC/SN and 36% of SCLC into 5 groups other than SN. In total, lung cancer can be divided into 9 molecular categories defined by distinct patterns of CD43 expression. We predict that this classification has clinically relevant predictive power.

The nuclear localization of the C-terminal domain of CD43 in lung cancer contrasts with colon cancer where it localizes predominantly to the cytoplasm [33]. This indicates that in lung cancer the C-terminal domain of CD43 is linked to its bipartite nuclear localization signal while in colon cancer it is not.

Example 5

Characterization of Aggressiveness of Cancer

Formalin-fixed paraffin-embedded tumors isolated from 84 patients with breast cancer were analyzed for their intracellular pattern of CD43 expression. Patients were diagnosed at Gundersen Lutheran Medical Center, La Crosse, Wis. between 1980 and 2007. Disease stage ranged between 0 and IV.

The extent to which individual tumors stained in the cytoplasm or nucleus with the anti-CD43 antibodies L10 and SSGZ was scored either at 0 or 1+, as described above. Tumors were classified into the following three groups defined by their pattern of L10 and SSGZ staining in the nucleus and cytoplasm:

LCN/SN: Tumors exhibiting a L10 staining score of 1+ in both the nucleus and cytoplasm together with a SSGZ staining score of 1+ in the nucleus and 0 in the cytoplasm.

LC/SN: Tumors exhibiting a L10 staining score of 0 in the nucleus but 1+ in the cytoplasm together with a SSGZ staining score of 1+ in the nucleus and 0 in the cytoplasm.

SN: Tumors exhibiting a L10 staining score of 0 in both the nucleus and cytoplasm together with a SSGZ staining score of 1+ in the nucleus but 0 in the cytoplasm.

The other L10 and SSGZ staining patterns described in the example above (i.e., LC/SC, LC, LN, LCN, SCN, and 4NG) were rarely, if ever, observed in the breast cancer tissue of the present example.

TABLE 2

Molecular classification of breast cancer aggressiveness based on intracellular patterns of CD43 expression defined by combinations of SSGZ and L10 antibody staining.

| CD43 Staining Pattern | Survival (years) | | % > 5 Years Survival |
|---|---|---|---|
| | <5 | >5 | |
| LCN/SN | 7 Cases | 30 Cases | 81% |
| LC/SN | 10 Cases | 20 Cases | 67% |
| SN | 6 Cases | 6 Cases | 50% |

As shown in Table 2, patients with tumors stained by SSGZ in the nucleus have decreasing overall survival depending on the extent of intracellular staining of L10. Therefore, the intracellular pattern of CD43 expression appears to predict patient survival, thereby serving as a biomarker to determine treatment.

Example 6

Conclusions

The above data reveal new molecular categories of cancer defined using the SSGZ antibody either alone or in combination with other antibodies or other molecular reagents. The invention extends to the use of SSGZ, the peptide of 26 amino acids to which it binds, and the DNA sequence encoding this peptide in screening, diagnostic and/or predictive kits.

CITED REFERENCES

1. Ostberg J R, Barth R K, Frelinger J G. The Roman god Janus: A paradigm for the function of CD43. *Immunol Today.* 1998; 19:456-550.
2. Rosenstein Y, Santana A, Pedraza-Alva G. CD43, a molecule with multiple functions. *Immunol Res.* 1999; 20:89-99.
3. Pallant A, Ezkenazi A, Mattei M-G, Fournier R E K, Carlsson S R, Fukuda M, Frelinger J G. Characterization of cDNAs encoding human leukosialin and localization of the leukosialin gene to chromosome 16. *Proc Natl Acad Sci USA.* 1989; 86:1328-32.
4. Shelley C S, Remold-O'Donnell E, Davis A E, III, Bruns G A P, Rosen F S, Carroll M C, Whitehead A S. Molecular characterization of sialophorin (CD43), the lymphocyte surface sialoglycoprotein defective in Wiskott-Aldrich syndrome. *Proc Natl Acad Sci USA.* 1989; 86:2819-28.
5. Cyster J G, Shotton D M, Williams A F. The dimensions of the T-lymphocyte glycoprotein leukosialin and identification of linear protein epitopes that can be modified by glycosylation. *EMBO J.* 1991; 10:893-902.
6. Hernandez J D, Nguyen J T, He J, Wang W, Ardman B, Green J M, Fukuda M, Baum L G. Galectin-1 binds different CD43 glycoforms to cluster CD43 and regulate T cell death. *J. Immunol.* 2006; 177:5328-36.
7. Brown T J, Shuford W W, Wang W-C, Nadler S G, Baily T S, Marquardt H, Mittler R S. Characterization of a CD43/leukosialin-mediated pathway for inducing apoptosis in human T-lymphoblastoid cells. *J Biol. Chem.* 1996; 271: 27686-95.
8. He Y-W, Bevan M J. High level expression of CH43 inhibits T cell receptor/CD3-mediated apoptosis. *J Exp Med.* 1999; 190:1903-8.
9. Todeschini A R, Nunes M P, Pires R S, Lopes M F, Previato J O, Mendonca-Previato L, DosReis G A. Costimulation of host T lymphocytes by a trypanosomal trans-sialidase: Involvement of CD43 signaling. *J. Immunol.* 2002; 168: 5192-8.
10. Kim H J, Park H J, Park W S, Bae Y. CH43 cross-linking increases the Fas-induced apoptosis through induction of Fas aggregation in Jurkat T-cells. *Exp Mol. Med.* 2006; 38:357-63.
11. Brown W R A, Barclay A N, Sunderland C A, Williams A F. Identification of a glycoprotein-like molecule at the cell surface of rat thymocytes. *Nature.* 1981; 289:456-60.
12. Ardman B, Sikorski M A, Staunton D E. CD43 interferes with T-lymphocyte adhesion. *Proc Natl Acad Sci USA.* 1992; 89:5001-5.
13. Soler M, Merant C, Servant C, et al. Leukosialin (CD43) behavior during adhesion of human monocytic THP-1 cells to red blood cells. *J Leukoc Biol.* 1997; 61:609-18.
14. Fukuoka M, Fukudome K, Yamashita Y, Tokushima M, Miyake K, Kimoto M. Antiadhesive function of 130-kd glycoform of CD43 expressed in CD4 T-lymphocyte clones and transfectant cell lines. *Blood.* 2000; 96:4267-75.
15. Rosenstein Y, Park J K, Hahn W C, Rosen F S, Bierer B E, Burakoff S J. CD43, a molecule defective in Wiskott-Aldrich syndrome, binds ICAM-1. *Nature.* 1991; 354:233-5.
16. Stockl J, Majdic O, Kohl P, Pickl W F, Menzel J E, Knapp W. Leukosialin (CD43)-major histocompatibility class I molecule interactions involved in spontaneous T cell conjugate formation. *J Exp Med.* 1996; 184:1769-79.
17. van den Berg T K, Nath D, Ziltener H J, Vestweber D, Fukuda M, van Die I, Crocker P R. Cutting edge: CD43 functions as a T cell counterreceptor for the macrophage adhesion receptor sialoadhesin (Siglec-1). *J. Immunol.* 2001; 166:3637-40.
18. Matsumoto M, Atarashi K, Umemoto E, Furukawa Y, Shigeta A, Miyasaka M, Hirata T. CD43 functions as a ligand for E-selectin on activated T cells. *J. Immunol.* 2005; 175:8042-50.
19. Remold-O'Donnell E, Rosen F S. Proteolytic fragmentation of sialophorin (CD43). Localization of the activation-inducing site and examination of the role of sialic acid. *J. Immunol.* 1990; 145:3372-8.
20. Campanero M R, Pulido R, Alonso J L, Pivel J P, Pimentel-Muinos F X, Fresno M, Sanchez-Madrid F. Downregulation by tumor necrosis factor-α of neutrophil cell surface expression of the sialophorin CD43 and the hyaluronate receptor CD44 through a proteolytic mechanism. *Eur J. Immunol.* 1991; 21:3045-8.
21. Bazil V, Strominger J L. CD43, the major sialoglycoprotein of human leukocytes, is proteolytically cleaved from the surface of stimulated lymphocytes and granulocytes. *Proc Natl Acad Sci USA.* 1993; 90:3792-6.
22. Mambole A, Baruch D, Nusbaum P, Bigot S, Susuki M, Lesavre P, Fukuda M, Halbwachs-Mecarelli L. The cleavage of neutrophil leukosialin (CD43) by cathepsin G releases its extracellular domain and triggers its intramembrane proteolysis by presenilin/γ-secretase. *J Biol. Chem.* 2008; 283:23627-35.
23. Seo W, Ziltener H J. CD43 processing and nuclear translocation of CD43 cytoplasmic tail are required for cell homeostasis. *Blood.* 2009; 114:3567-77.
24. Da Silva N, Bharti A, Shelley C S. HnRNP-K and Purα act together to repress the transcriptional activity of the CD43 gene promoter. *Blood.* 2002; 100:3536-44.
25. Shelley C S, Da Silva N, Teodoridis J M. During U937 monocytic differentiation repression of the CD43 gene promoter is mediated by the single-stranded DNA binding protein Purα. *Br J. Haematol.* 2001; 115:159-66.
26. Sánchez-Mateos P, Campanero M R, del Pozo M A, Sánchez-Madrid F. Regulatory role of CD43 leukosialin on integrin-mediated T-cell adhesion to endothelial and extracellular matrix ligands and its polar redistribution to a cellular uropod. *Blood.* 1995; 86:2228-39.
27. Serrador J M, Nieto M, Alonso-Lebrero J L, del Pozo M A, Calvo J, Furthmayr H, Schwartz-Albiez, R, Lozano F, González-Amaro R, Sánchez-Mateos P, Sánchez-Madrid, F. CD43 interacts with moesin and ezrin and regulates its redistribution to the uropods of T lymphocytes at the cell-cell contacts. *Blood.* 1998; 91:4632-44.
28. Sabri S, Soler M, Foa C, Pierres A, Benoliel A, Bongrand P. Glycocalyx modulation is a physiological means of regulating cell adhesion. *J Cell Sci.* 2000; 113:1589-600.
29. Seveau S, Keller H, Maxfield F R, Piller F, Halbwachs-Mecarelli L. Neutrophil polarity and locomotion are associated with surface redistribution of leukosialin (CD43), an antiadhesive membrane molecule. *Blood.* 2000; 95:2462-70.
30. Piller F, Piller V, Fox R I, Fukuda M. Human T-lymphocyte activation is associated with changes in O-glycan biosynthesis. *J Biol. Chem.* 1988; 263:15146-50.
31. Tomlinson-Jones A, Federsppiel B, Ellies L G, Williams M J, Burgener R, Duronio V, Smith C A, Takei F, Ziltener H J. Characterization of the activation-associated isoform of CD43 on murine T lymphocytes. *J. Immunol.* 1994; 153:3426-39.
32. Sikut R, Nilsson O, Baeckstrom D, Hansson G C. Colon adenoma and cancer cells aberrantly express the leukocyte-associated sialoglycoprotein CD43. *Biochem Biophys Res Comm.* 1997; 238:612-6.
33. Sikut R, Andersson C X, Sikut A, Fernandez-Rodriguez J, Karlsson N G, Hansson G C. Detection of CD43 (leukosialin) in colon adenoma and adenocarcinoma by novel monoclonal antibodies against its intracellular domain. *Int J. Cancer.* 1999; 82:52-8.
34. Woo V L, Bhuiya T, Kelsch R. Assessment of CD43 expression in adenoid cystic carcinomas, polymorphous low-grade adenocarcinomas, and monomorphic adenomas. *Oral Surg Oral Med Oral Pathol Oral Radiol Endod.* 2006; 102:495-500.
35. Seethala R R, Pasha T L, Raghunath P N, LiVolsi V A, Zhang P J. The selective expression of CD43 in adenoid cystic carcinoma. *Appl Immunohistochem Mol. Morphol.* 2008; 16:165-72.
36. Ioachim H L, Pambuccian S, Giancotti F, Dorsett B. Reactivity of lung tumors with lung-derived and non-lung-derived monoclonal antibodies. *Int J Cancer: Suppl.* 1994; 8:132-3.
37. Santamarla M, LOpez-Beltran A, Toro M, Peria J, Molina U. Specific monoclonal antibodies against leukocyte-restricted cell surface molecule CD43 react with nonhematopoietic tumor cells. *Cancer Res.* 1996; 56:3526-9.
38. Subramanian J, Simon R. Gene expression-based prognostic signatures in lung cancer: Ready for clinical use? *J Natl Cancer Inst.* 2010; 102:464-74.

39. Andersson C X, Fernandez-Rodriguez J, Laos S, Sikut R, Sikut, A, Baeckstrom D, Hansson G C. CD43 has a functional NLS, interacts with β-catenin, and affects gene expression. *Biochem Biophys Res Commun.* 2004; 316:12-7.

40. Remold-O'Donnell E, Kenney D M, Parkman R, Cairns L, Savage B, Rosen F S. Characterization of a human lymphocyte surface sialoglycoprotein that is defective in Wiskott-Aldrich syndrome. *J Exp Med.* 1984; 159:1705-23.

What is claimed is:

1. A method of characterizing and/or treating cancerous tissue comprising:
   contacting cancerous tissue with a first antibody in a format capable of resolving nuclear binding and cytoplasmic binding, wherein the first antibody is an antibody capable of specifically binding cytoplasmic tail of CD43 in the format;
   contacting the tissue with a second antibody in the format capable of resolving nuclear binding and cytoplasmic binding, wherein the second antibody is an antibody capable of specifically binding extracellular domain of CD43; and
   resolving cellular localization of any binding to the tissue with the first antibody and the second antibody, wherein nuclear binding with the first antibody, a lack of cytoplasmic binding with the first antibody, a lack of nuclear binding with the second antibody, and a lack of cytoplasmic binding with the second antibody characterizes the tissue as being more aggressively cancerous than tissue not showing nuclear binding with the first antibody, a lack of cytoplasmic binding with the first antibody, a lack of nuclear binding with the second antibody, and a lack of cytoplasmic binding with the second antibody.

2. The method of claim 1 wherein the first antibody is capable of specifically binding at least a portion of a polypeptide consisting of sequence WRRRQKRRTGALVLSRG-GKRNGVVDAWAGPAQVPEE-GAVTVTVGGSGGDKGSGFPD GEGSSRRPTLTTFFGRRK-SRQGSLAMEELKSGSGPSLKGEEE-PLVASEDGAVDAPAPDEP EGGDGAAP (residues 277-400 of SEQ ID NO:1).

3. The method of claim 1 wherein the first antibody is capable of specifically binding at least a portion of a polypeptide consisting of sequence PLVASEDGAVDAPAPDEPEG-GDGAAP (residues 375-400 of SEQ ID NO:1).

4. The method of claim 1 wherein the second antibody is capable of specifically binding at least a portion of a polypeptide consisting of sequence STTAVQTPTSG EPLVSTSE-PLSSKMYTTSITSDPKADSTGDQT-SALPPSTSINEGSPLWTSIGASTGSPLPEPT TYQEVSIKMSSVPQETPHATSHPAVPI-TANSLGSHTVTGGTITTNSPETSSRTSGAPVTTA ASS-LETSRGTSGPPLTMATVSLETSKGTSGP-PVTMATDSLETSTGTTGPPVTMTTGSLEPS SGASGPQVSSVKLSTMMSPTTSTNAS-TVPFRNPDENSR (residues 20-253 of SEQ ID NO:1).

5. The method of claim 1 wherein nuclear binding with the first antibody, a lack of cytoplasmic binding with the first antibody, a lack of nuclear binding with the second antibody, and a lack of cytoplasmic binding with the second antibody indicates decreased rates of survival of a patient providing the tissue compared to survival of a patient providing tissue not characterized by nuclear binding with the first antibody, a lack of cytoplasmic binding with the first antibody, a lack of nuclear binding with the second antibody, and a lack of cytoplasmic binding with the second antibody.

6. The method of claim 1 wherein nuclear binding with the first antibody, a lack of cytoplasmic binding with the first antibody, a lack of nuclear binding with the second antibody, and a lack of cytoplasmic binding with the second antibody indicates decreased rates of survival of a patient providing the tissue compared to survival of a patient providing tissue characterized by nuclear binding with the first antibody and at least cytoplasmic binding with the second antibody.

7. The method of claim 1 wherein nuclear binding with the first antibody, a lack of cytoplasmic binding with the first antibody, a lack of nuclear binding with the second antibody, and a lack of cytoplasmic binding with the second antibody indicates decreased rates of survival of a patient providing the tissue compared to survival of a patient providing tissue characterized by nuclear binding with the first antibody, cytoplasmic binding with the second antibody, and nuclear binding with the second antibody.

8. The method of claim 1 wherein nuclear binding with the first antibody, a lack of cytoplasmic binding with the first antibody, cytoplasmic binding with the second antibody, and a lack of nuclear binding with the second antibody indicates decreased rates of survival of a patient providing the tissue compared to survival of a patient providing tissue characterized by nuclear binding with the first antibody, cytoplasmic binding with the second antibody, and nuclear binding with the second antibody.

9. A method of characterizing and/or treating cancerous tissue comprising:
   contacting cancerous tissue with a first antibody in a format capable of resolving nuclear binding and cytoplasmic binding, wherein the first antibody is an antibody capable of specifically binding cytoplasmic tail of CD43 in the format;
   contacting the tissue with a second antibody in the format capable of resolving nuclear binding and cytoplasmic binding, wherein the second antibody is an antibody capable of specifically binding extracellular domain of CD43; and
   resolving cellular localization of any binding to the tissue with the first antibody and the second antibody, wherein nuclear binding with the first antibody, a lack of cytoplasmic binding with the first antibody, a lack of nuclear binding with the second antibody, and a lack of cytoplasmic binding with the second antibody characterizes the tissue as being more aggressively cancerous than tissue not showing nuclear binding with the first antibody, a lack of cytoplasmic binding with the first antibody, a lack of nuclear binding with the second antibody, and a lack of cytoplasmic binding with the second antibody, wherein the tissue is selected from the group consisting of lung tissue and breast tissue.

10. The method of claim 9 wherein the tissue is lung tissue and wherein nuclear binding with the first antibody, a lack of cytoplasmic binding with the first antibody, a lack of nuclear binding with the second antibody, and a lack of cytoplasmic binding with the second antibody characterizes the tissue as probable small cell lung cancer tissue.

11. The method of claim 9 wherein the tissue is lung tissue and wherein cytoplasmic binding with the second antibody characterizes the tissue as probable non-small cell lung cancer tissue.

12. The method of claim 9 wherein the tissue is lung tissue and wherein nuclear binding with the first antibody and cytoplasmic binding with the second antibody characterizes the tissue as probable non-small cell lung cancer tissue.

13. The method of claim 9 wherein the tissue is lung tissue and wherein nuclear binding with the first antibody, cytoplasmic binding with the second antibody, and nuclear binding with the second antibody characterizes the tissue as probable non-small cell lung cancer tissue.

14. The method of claim 1 further comprising treating a patient providing the tissue based on the resolved cellular localization of any binding with the first antibody and the second antibody to the tissue.

15. The method of claim 9 further comprising characterizing the tissue as probable small cell lung cancer tissue and treating a patient providing the tissue with a small lung cancer cell-specific treatment.

16. The method of claim 9 further comprising characterizing the tissue as probable non-small cell lung cancer tissue and treating a patient providing the tissue with a non-small lung cancer cell-specific treatment.

17. A method of characterizing and/or treating cancerous tissue comprising:
   contacting cancerous lung tissue with a first antibody in a format capable of resolving nuclear binding and cytoplasmic binding, wherein the first antibody is an antibody capable of specifically binding cytoplasmic tail of CD43 in the format;
   contacting the tissue with a second antibody in the format capable of resolving nuclear binding and cytoplasmic binding, wherein the second antibody is an antibody capable of specifically binding extracellular domain of CD43; and
   resolving cellular localization of any binding to the tissue with the first antibody and the second antibody, wherein:
      nuclear binding with the first antibody, a lack of cytoplasmic binding with the first antibody, a lack of nuclear binding with the second antibody, and a lack of cytoplasmic binding with the second antibody characterizes the tissue as probable small cell lung cancer tissue; or
      cytoplasmic binding with the second antibody characterizes the tissue as probable non-small cell lung cancer tissue.

18. The method of claim 17 wherein nuclear binding with the first antibody and cytoplasmic binding with the second antibody characterizes the tissue as probable non-small cell lung cancer tissue.

19. The method of claim 17 wherein nuclear binding with the first antibody, cytoplasmic binding with the second antibody, and nuclear binding with the second antibody characterizes the tissue as probable non-small cell lung cancer tissue.

* * * * *